(12) United States Patent
Roulier et al.

(10) Patent No.: US 6,391,322 B1
(45) Date of Patent: May 21, 2002

(54) COMPOSITION IN THE FORM OF A W/O EMULSION WITH A HIGH CONTENT OF WAX AND ITS USES IN THE COSMETICS AND DERMATOLOGICAL FIELDS

(75) Inventors: Veronique Roulier, Paris; Therese Daubige, Mousseaux les Bray, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/453,470

(22) Filed: Dec. 2, 1999

(30) Foreign Application Priority Data

Dec. 3, 1998 (FR) .............................. 98 15292

(51) Int. Cl.$^7$ ...................... A61K 7/021; A61K 7/025; A61K 7/06; A61K 7/00
(52) U.S. Cl. .................... 424/401; 424/63; 424/64; 424/70.1; 424/70.7; 424/400; 514/844; 514/937; 516/21; 516/23
(58) Field of Search ................. 424/400, 401, 424/63, 64, 70.1, 70.7; 514/844, 937; 516/21, 23

(56) References Cited

U.S. PATENT DOCUMENTS

| 5,250,289 A | * | 10/1993 | Boothroyd et al. ........... 424/59 |
| 5,362,482 A | | 11/1994 | Yoneyama et al. |
| 5,523,091 A | * | 6/1996 | Pastour et al. ............... 424/401 |
| 5,851,539 A | * | 12/1998 | Mellul et al. ............... 424/401 |
| 5,863,544 A | * | 1/1999 | Willcox et al. ............. 424/401 |
| 5,935,589 A | * | 8/1999 | Mukherjee et al. ......... 424/401 |
| 5,939,054 A | * | 8/1999 | Msika et al. .................. 424/59 |
| 5,942,213 A | * | 8/1999 | Bara et al. ..................... 424/63 |
| 5,961,998 A | * | 10/1999 | Arnaud et al. .............. 424/401 |
| 5,972,315 A | * | 10/1999 | Voss et al. ..................... 424/59 |
| 6,015,548 A | * | 1/2000 | Siddiqui et al. .............. 424/59 |
| 6,051,211 A | * | 4/2000 | Hansenne et al. ............ 424/59 |

FOREIGN PATENT DOCUMENTS

| EP | 0 152 953 A2 | | 8/1985 |
| EP | 667 146 | * | 1/1995 |

OTHER PUBLICATIONS

Concise Encyclopedia of Chemistry, 1994, p. 651.*
Hawley's COndensed Chemical Dictionary, 1997, p. 753.*

* cited by examiner

*Primary Examiner*—José G. Dees
*Assistant Examiner*—Marina Lamm
(74) *Attorney, Agent, or Firm*—Oblon, Spivak, McClelland, Maier & Neustadt, P.C.

(57) ABSTRACT

The present invention relates to a composition in the form of a cream composed of a water-in-oil emulsion, wherein it includes at least 25% by weight of an aqueous phase with respect to the total weight of the composition, at least one silicone emulsifier and at least 5% by weight of one or more waxes with respect to the total weight of the composition. The present invention also relates to the uses of the above composition in the cosmetics and dermatological fields, in particular in caring for, treating and/or making up the skin and/or mucous membranes and more particularly in treating wrinkles and/or fine lines of the skin and/or in treating dry skin. The invention also relates to a process for the preparation of the above composition, wherein at least one stage of the process is carried out using a mixer-extruder.

19 Claims, No Drawings

COMPOSITION IN THE FORM OF A W/O EMULSION WITH A HIGH CONTENT OF WAX AND ITS USES IN THE COSMETICS AND DERMATOLOGICAL FIELDS

BACKGROUND OF THE INVENTION

1. Field of the Invention

The present invention relates to a composition in the form of a cream composed of a water-in-oil (W/O) emulsion having a high content of wax and to its uses in the cosmetics and dermatological fields. The invention also relates to methods of for caring for, treating and/or making up the skin and/or mucous membranes, and more particularly in the treatment of wrinkles and/or fine lines of the skin and/or in the treatment of dry skin. The invention also relates to a process for the preparation of the composition, wherein at least one stage of the process is carried out using a mixer-extruder.

2. Discussion of the Background

It is known to use waxes in cosmetic creams which are provided in the form of emulsions for caring for human skin, in particular for the anti-wrinkle effects of these waxes. Nevertheless, it is difficult to incorporate a high percentage of waxes in such compositions because waxes have a tendency to greatly thicken emulsions. In addition, when a high percentage of waxes is incorporated in an emulsion, the emulsion is very difficult to apply to the skin because it does not slip. Furthermore, a rough effect is produced on the skin. As a result, both the attractiveness and effective use of such an emulsion is significantly and undesirably reduced.

It is also known to incorporate a high percentage of waxes in mascaras. However, because of the above-mentioned disadvantages, compositions of this type cannot be used as a care product.

To prepare an emulsion that contains waxes, it is necessary to melt the e waxes in the fatty phase of the emulsion. This is particularly so if, for example, one wishes to use waxes having particularly advantageous anti-wrinkle effects on the skin, such as carnauba waxes. It is therefore necessary to heat the fatty phase to temperatures of 80–85° C., which is particularly harmful if one wishes to incorporate heat-sensitive compounds into the composition.

The need therefore remains for a composition having the consistency of a cream and containing a significant percentage of waxes without the disadvantages of the prior art.

Surprisingly, it has now been found that it is possible to incorporate a high percentage of waxes in creams in the form of W/O emulsions, while retaining satisfactory fluidity and a pleasant feeling during application on the skin, by preparing the emulsion under cold conditions using a silicone emulsifier and starting from a soft oily phase having a high percentage of waxes.

SUMMARY OF THE INVENTION

Thus, one object of the present invention is to provide a composition having the consistency of a cream.

Another object of the invention is to provide a composition having a significant percentage of waxes without the above-mentioned disadvantages.

Another object of the invention is to provide a composition having a high percentage of waxes in creams in the form of W/O emulsions.

Another object of the invention is to provide a composition having satisfactory fluidity and a pleasant feeling during application on the skin, These and other objects of the invention have been achieved by the present invention, the first embodiment of which provides a composition in the form of a cream composed of a water-in-oil emulsion that includes an aqueous phase dispersed in an oily phase, wherein it includes at least 25% by weight of an aqueous phase with respect to the total weight of the composition, at least one silicone emulsifier and at least 5% by weight of one or more waxes with respect to the total weight of the composition.

Another embodiment of the invention provides a cosmetic and/or dermatological composition, that includes the above composition.

Another embodiment of the invention provides a method of treating, protecting, caring for and/or cleansing the skin, mucous membranes and/or hair and/or in making up the skin and/or mucous membranes, that includes applying to the skin, mucous membranes and/or hair the above composition.

Another embodiment of the invention provides a method of treating wrinkles and/or fine lines of the skin, that includes applying to the skin the above composition.

Another embodiment of the invention provides a method of treating and/or protecting dry skin, that includes applying to the skin the above composition.

Another embodiment of the invention provides a process for preparing the above composition, that includes at least one step using a screw mixer-extruder.

BRIEF DESCRIPTION OF THE PREFERRED EMBODIMENTS

Various other objects, features and attendant advantages of the present invention will be more fully appreciated as the same becomes better understood from the following detailed description of the preferred embodiments of the invention.

The composition of the invention is in the form of a cream, that is to say a soft product, in contrast to a solid product, such as a stick. In the context of the present invention, a cream preferably has a viscosity at ambient temperature (approximately 20–25° C.) ranging from approximately 1 to 25 Pa·s and preferably from approximately 1 to 10 Pa·s, this viscosity being measured with a Rheomat 180.

The composition of the invention, although containing a high level of wax, also contains a significant level of aqueous phase and is therefore fresh on application. In addition, since the mixing of the aqueous phase and the oily phase is carried out under cold conditions, heat-sensitive compounds can be incorporated without fear of their decomposition.

Preferably, the composition of the invention contains, in the oily phase, at least 5% by weight of one or more waxes with respect to the total weight of the composition. The cooled oily phase, before it is mixed with the aqueous phase, preferably exists in the form of a soft paste at ambient temperature (approximately 25° C.). The term "soft paste" is understood here to mean a paste for which the viscosity can be measured, in contrast to the solid structure of a tube or stick, for which the viscosity cannot be measured. The dynamic viscosity of the soft paste at 25° C. is generally between 3 and 35 Pa·s, measured with a Contraves TV rotary viscometer equipped with an "MS-r4" rotor at a frequency of 60 Hz.

Preferable waxes which can be used in the composition of the invention include, for example, mineral waxes, such as microcrystalline waxes, paraffin wax, petrolatum wax, petroleum wax, ozokerite or montan wax; animal waxes, such as beeswax, lanolin and its derivatives; vegetable waxes, such as candelilla, ouricurry, carnauba or japan waxes, cocoa butter, or cork fibre or sugar cane waxes; hydrogenated oils which are solid at 25° C.; fatty esters and glycerides which are solid at 25° C.; synthetic waxes, such as polyethylene waxes and waxes obtained by the Fischer-Tropsch synthesis; silicone waxes, and their mixtures.

According to a preferred embodiment of the invention, use is made of at least one wax having a starting melting temperature greater than or equal to 50° C. and better still at least one wax for which the starting melting temperature is greater than 65° C., such as carnauba wax, some polyethylene waxes and some microcrystalline waxes, such as that sold by the company Tisco under the name "Tisco Wax 881, or that sold by the company RMC under the name of "Feruwax 30540".

Preferably, the term "starting melting temperature" is understood to mean the temperature at which a wax begins to melt. This temperature can be determined by DTA (differential thermal analysis), which makes it possible to obtain a thermogram (or melt curve) of the wax under consideration. The starting melting temperature corresponds to the temperature at which a significant change of slope in the thermogram can be observed. The melting point, for its part, represents the minimum point in the thermogram.

The amount of wax(es) in the composition of the invention is at least 5% and preferably ranges from 5 to 30% and better still from 5 to 15% by weight with respect to the total weight of the composition. These ranges include all subranges and values therebetween.

The amount of oily phase containing at least one wax in the composition of the invention preferably ranges from 20 to 75% and more preferably from 30 to 60% by weight with respect to the total weight of the composition. These ranges include all subranges and values therebetween. Preferably, this oily phase is used in such an amount or else includes an amount of waxes such that the amount of waxes in the final composition is equal to or greater than 5%.

Preferably, the oily phase of the composition of the invention includes, in addition to the wax or waxes, one or more fatty substances chosen from oils of animal origin, oils of vegetable origin, mineral oils, synthetic oils, fluorinated oils, silicone oils, in particular volatile silicone oils, silicone gums, silicone resins, fatty alcohols, fatty acids and silicone elastomers, such as the products sold under the name "KSG" by the company Shin-Etsu, under the name "Trefil" by the company Dow Corning or under the name "Gransil" by the company General Electric.

The silicone emulsifier used in the composition of the invention is preferably chosen from the group including oxyethylenated and/or oxypropylenated polydimethylsiloxanes, oxyethylenated and/or oxypropylenated ($C_{10}$–$C_{22}$)alkylpolydimethylsiloxanes ("($C_{10}$–$C_{22}$) alkyl" meaning that the alkyl chain contains from 10 to 22 carbon atoms), oxyethylenated and/or oxypropylenated polydimethylsiloxanes with glucoside groups, and their mixtures. These polydimethylsiloxanes can optionally be crosslinked. Preferably, the above-noted glucoside groups are bonded to the oxyethylenated and/or oxypropylenated polydimethylsiloxanes according to methods within the ordinary skill of the artisan.

Preferably, the silicone emulsifier can be introduced as is or as a mixture with a volatile or non-volatile silicone oil, such as a cyclomethicone (cyclohexasiloxane, cyclopentasiloxane or cyclotetrasiloxane).

Mention may be made, as the most preferred silicone emulsifiers which can be used in the composition of the invention, of the mixtures of dimethicone copolyol and of cyclomethicone sold under the names "Q2-3225C" and "DC2-5225C" by the company Dow Corning, the product sold under the name "SF-1288" by the Company General Electric, the polyglyceryl-4 isostearate/cetyl dimethicone copolyol/hexyl laurate mixture sold under the name "Abil WE 09" by the company Goldschmidt, the cetyl dimethicone copolyol sold under the name "Abil EM 90" by the company Goldschmidt, or the laurylmethicone copolyol sold under the name "Q2-5200" by the company Dow Corning.

The amount of silicone emulsifier in the composition according to the invention preferably ranges from 0.1 to 10% by weight as active material and more preferably from 2 to 5% by weight as active material with respect to the total weight of the composition. These ranges include all subranges and values therebetween.

The composition of the invention may additionally, and optionally, include one or more fillers (pulverulent constituents) which can be chosen, for example, from the group including talc; micas of natural or synthetic origin; kaolin; zinc or titanium oxides; calcium carbonate; magnesium carbonate and hydrocarbonate; silica, in particular spherical silica, silica powder, sold under the name "Cab-O-Sil TS 5301, by the company Cabot, and silica microbeads, such as those sold under the name SB 150 by the company Myoshi; titanium dioxide; glass and ceramic beads sold by the company 3M under the trade name "Macrolite"; metal soaps derived from an organic carboxylic acid having from 8 to 22 carbon atoms, preferably from 12 to 18 carbon atoms, for example zinc, magnesium or lithium stearate, zinc laurate or magnesium myristate; powders formed from non-expanded synthetic polymers, such as powders formed from polyethylene, polystyrene, polyesters, polyamides (for example, Nylon or poly-β-alanine), acrylate copolymers (for example, the microporous microspheres sold by the company Dow Corning under the trade name "Polytrap"), poly(methacrylic acid)s, polystyrene or Teflon, such as "Fluon"; expanded powders, such as hollow microspheres made of thermoplastic material prepared by known processes, such as those disclosed in U.S. Pat. No. 3,615,972 and EP-A-056,219 (the entire contents of each of which are hereby incorporated by reference), and in particular the microspheres sold under the trade name "Expancel" by the company Kemanord Plast or under the trade name "Micropearl F 80 ED" by the company Matsumoto; powders formed from natural organic materials, such as maize, wheat or rice starches, which may or may not be crosslinked, such as the powders formed from starch crosslinked by octenylsuccinic anhydride sold under the name "Dry-Flo" by the company National Starch; silicone resin microbeads, such as those sold under the name "Tospearl" by the company Toshiba Silicone, and their mixtures.

Preferably, the fillers can represent up to 20% by weight with respect to the total weight of the composition and more preferably from 1 to 12% by weight with respect to the total weight of the composition. These ranges include all subranges and values therebetween.

The aqueous phase of the composition of the invention represents at least 25% by weight with respect to the total weight of the composition and preferably from 40 to 70% by weight with respect to the total weight of the composition. These ranges include all subranges and values therebetween.

The composition according to the invention can be used in any field where this type of pharmaceutical dosage form is advantageous and in particular in the cosmetics and dermatological fields. When it constitutes a cosmetic and/or dermatological composition, it may additionally include a physiologically acceptable medium, that is to say a medium which is compatible with the skin, mucous membranes, nails and/or hair.

Preferably, the compositions of the invention are especially suited for a large variety of treatments of the skin, mucous membranes (lips) and hair, including the scalp, in particular in protecting, caring for, cleansing and/or making up the skin and/or mucous membranes, in protecting, caring for and/or cleansing the hair and/or in the treatment of the skin, hair and/or mucous membranes.

The compositions according to the invention can be used, for example, as products for treating, caring for, protecting and/or cleansing the skin, in the form of creams or milks, or as (skin and lip) makeup products by incorporating fillers and/or coloring materials (pigments and/or dyes). They are particularly appropriate in the treatment of wrinkles and/or fine lines of the skin and in the treatment and/or protection of dry skin.

Another preferred embodiment of the invention relates to the cosmetic use of the composition as defined above in treating, protecting, caring for and/or cleansing the skin, mucous membranes and/or hair and/or in making up the skin and/or mucous membranes.

Another preferred embodiment of the invention relates to the cosmetic use of the composition as defined above in treating wrinkles and/or fine lines of the skin.

Another preferred embodiment of the invention relates to the use of the composition as defined above in the manufacture of a composition intended for treating and/or protecting dry skin.

In addition, and in a known way, the composition of the invention can additionally, and optionally, include adjuvants which are conventional in the cosmetics or dermatological field, such as hydrophilic or lipophilic active principles, preservatives, antioxidants, fragrances, solvents, sunscreen agents, coloring materials, basic or acidic agents, and lipid vesicles. These adjuvants are preferably used in the proportions which are conventional in the cosmetics or dermatological field, for example from 0.01 to 30% of the total weight of the composition, and they are, depending in their nature, introduced into the aqueous phase or into the oily phase of the composition or alternatively into vesicles. These adjuvants and their concentrations must be such that they do not modify the property desired for the composition.

Mention may be made, as preferred active principles which can be used in the composition of the invention, of, for example, moisturizing agents, such as polyols and in particular glycerol, ethylene glycol, isoprene glycol, 1,2-propanediol, diglycerol, sorbitol, polyethylene glycols and their mixtures.

Preferably, the composition according to the invention can advantageously be prepared by using, for at least one stage of the process, a kneading device, such as a roll-mill mixer comprising two rollers rotating in opposite directions, between which the paste passes, or a screw mixer-extruder. Use is preferably made of a screw mixer-extruder. More preferably, this step includes mixing and extruding or rolling and milling at least one or more of the constituent components of the composition of the invention, including the aqueous phase, the oily phase, the silicone emulsifier, or the wax(es), or mixtures thereof. Most preferably, the step includes mixing and extruding the wax(es) and the oils.

Another preferred embodiment of the invention provides a process for the preparation of a composition according to the invention, wherein at least one stage of the process is carried out using a screw mixer-extruder.

Preferably, according to a first embodiment of the invention, the preparation process includes the following stages:

(1) preparation of the oily phase in the form of a soft paste obtained by forming a premix of the waxes and oils, by heating this premix to a temperature at which it melts to form a molten premix, introducing the molten premix and preferably other constituents (most preferably the fillers) of the oily phase, all at once or in several portions, into a screw mixer-extruder and subjected to a temperature gradient ranging from 80° C. to 20° C. to form a mixture, kneading the mixture thus obtained while cooling it to ambient temperature while conveying it to the outlet of the mixer-extruder;

(2) incorporation of the silicone emulsifier into the soft paste obtained in (1); and (3) incorporation, with stirring, of the aqueous phase into the mixture obtained in (2).

In the above-mentioned first embodiment, stages (2) and (3) are preferably carried out in a mixing device commonly used by a person skilled in the art, such as a rotor-stator.

Moreover, in the process described above, the amounts used are such that the emulsion obtained contains at least 5% by weight of wax and at least 25% by weight of aqueous phase, with respect to the total weight of the composition.

As indicated above, since the mixing of the oily and aqueous phases takes place under cold conditions, the incorporation of heat-sensitive compounds does not present a problem.

According to a most preferred embodiment of the invention, stages (2) and (3) above are also carried out in the screw mixer-extruder used for stage (1). The silicone emulsifier and the aqueous phase are then introduced into a part (or section) of the mixer-extruder where the temperature is close to ambient temperature.

The use of a mixer-extruder makes it possible to reproducibly obtain an oily phase paste of consistently high quality. In addition, it is possible, by adapting the outlet die of the mixer-extruder, to package the composition in line at the outlet of the said mixer-extruder.

Preferably, the various stages of the process can be carried out in one or more extruders arranged one after the other and more preferably in a single twin-screw extruder.

The preferred conditions under which the extrusion can be carried out are disclosed in the document FR-A2,715,306, the entire contents of which are hereby incorporated by reference.

EXAMPLES

Having generally described this invention, a further understanding can be obtained by reference to certain specific examples which are provided herein for purposes of illustration only and are not intended to be limiting unless otherwise specified. The amounts shown are percentages by weight.

EXAMPLE

Care Cream

Oily phase

| | |
|---|---|
| Dry-Flo (filler) | 7% |
| Microcrystalline wax | 19% |
| Mineral oil q.s. for | 100% |

W/O emulsion

| | |
|---|---|
| Oily phase | 40% |
| Dimethicone copolyol/cyclomethicone (Q2-3225C) | 10% |
| Water q.s. for | 100% |

Procedure 1:

The mixture of wax and of oil is heated to approximately 100° C.,
  the molten mixture is introduced into a mixer-extruder at the same time as the filler and the oily phase is obtained at the outlet of the mixer-extruder in the form of a soft paste,
  the silicone emulsifier is incorporated in the soft paste in a rotor-stator,
  the water is added little by little to the mixture while stirring.

Procedure 2:

The mixture of wax and of oil is heated to approximately 100° C.,
  the filler is introduced into the head section of a mixer-extruder having at least six sections,
  the oily phase is introduced into the second section of the screw mixer-extruder, and
  the aqueous phase and the silicone emulsifier are introduced, via two different inlets, into the fourth section of the screw mixer-extruder.

The sections of the screw mixer-extruder used are, ranging from the first to the sixth section, brought respectively to the following temperatures: 20° C., 80° C., 60° C., 20° C., 20° C., and 20° C.

A cream is obtained which exhibits a very light texture and which has good moisturizing qualities and is capable of smoothing the relief of the skin.

This application is based on French Application 98 15292, filed Dec. 3, 1998, the entire contents of which are hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed is:

1. A composition in the form of a cream, comprising:
   a water-in-oil emulsion comprising an aqueous phase dispersed in an oily phase,
   wherein the aqueous phase is present in an amount of at least 25% by weight with respect to the total weight of the composition,
   at least one silicone emulsifier; and
   at least 5% by weight of one or more waxes, with respect to the total weight of the composition, and wherein
   the oily phase, before it is mixed with the aqueous phase, is in the form of a soft paste at ambient temperature and is obtained by mixing the constituents of the oily phase to obtain a mixture and kneading said mixture while cooling it to ambient temperature and conveying it to an outlet of a mixer-extruder.

2. The composition according to claim 1, wherein the silicone emulsifier is selected from the group consisting of oxyethylenated polydimethylsiloxanes, oxypropylenated polydimethylsiloxanes, oxyethylenated and oxypropylenated polydimethylsiloxanes, oxyethylenated ($C_{10}$–$C_{22}$) alkylpolydimethysiloxanes, oxypropylenated ($C_{10}$–$C_{22}$) alkylpolydimethysiloxanes, oxyethylenated and oxypropylenated ($C_{10}$–$C_{22}$) alkylpolydimethysiloxanes, oxyethylenated polydimethysiloxanes with glucoside groups, oxypropylenated polydimethysiloxanes with glucoside groups, oxyethylenated and oxypropylenated polydimethysiloxanes with glucoside groups, and mixtures thereof.

3. The composition according to claim 1, wherein the silicon emulsifier is present in an amount of 0.1 to 10% by weight with respect to the total weight of the composition.

4. The composition according to claim 1, wherein the wax is selected from the group consisting of mineral waxes, animal waxes, vegetable waxes, hydrogenated oils which are solid at 25 ° C., fatty esters and glycerides which are solid at 25 ° C., synthetic waxes, and silicone waxes, and mixtures thereof.

5. The composition according to claim 1, wherein the wax has a starting melting temperature greater than or equal to 50° C.

6. The composition according to claim 1, wherein the amount of wax ranges from 5 to 30% by weight with respect to the total weight of the composition.

7. The composition according to claim 1, wherein the oily phase is present in an amount ranging from 20 to 75% by weight with respect to the total weight of the composition.

8. The composition according to claim 1, wherein the oily phase further comprises one or more fatty substances selected from the group consisting of oils of animal origin, oils of vegetable origin, mineral oils, synthetic oils, fluorinated oils, silicone oils, volatile silicone oils, silicone gums, silicone resins, fatty alcohols, fatty acids and silicone elastomers.

9. The composition according to claim 1, further comprising at least one filler.

10. The composition according to claim 9, wherein the filler is present in an amount ranging from 1 to 12% by weight with respect to the total weight of the composition.

11. The composition according to claim 1, wherein the aqueous phase is present in an amount ranging from 40 to 70% by weight with respect to the total weight of the composition.

12. A cosmetic and/or dermatological composition, comprising the composition according to claim 1.

13. A method of treating the skin, mucous membranes or hair, protecting the skin, mucous membranes or hair, caring for the skin, mucous membranes or hair cleansing the skin, mucous membranes and hair, or in making up the skin or mucous membranes, comprising applying to the skin, mucous membranes or hair the composition according to claim 1.

14. A method of treating wrinkles and/or fine lines of the skin, comprising applying to the skin the composition according to claim 1.

15. A method of treating and/or protecting dry skin, comprising applying to the skin the composition according to claim 1.

16. A process for preparing the composition according to claim 1, comprising:
   mixing and extruding at least a part of the composition of claim 1 in a screw mixer-extruder.

17. The process according to claim 16, further comprising the following stages:
   (1) preparing the oily phase in the form of a soft paste by forming a premix of at least one wax and at least one oil, heating the premix to a temperature at which it melts to form a molten premix, introducing the molten premix and, optionally, other constituents of the oily phase, optionally all at once or in more than one portion, into a screw mixer-extruder having a temperature gradient ranging from 80° C. to 20° C. to form a first mixture, kneading the thus obtained first mixture while cooling it to ambient temperature and conveying it to an outlet of the mixer-extruder;

(2) incorporating the silicone emulsifier into the soft paste obtained in (1) to form a second mixture; and (3) incorporating, with stirring, the aqueous phase into the second mixture obtained in (2).

18. The process according to claim 17, wherein stages (2) and (3) are carried out in the screw mixer-extruder of stage (1).

19. The process according to claim 17, wherein the soft paste has a dynamic viscosity at 25° C. of between 3 and 35 Pa·s, as measured with a Contraves TV rotary viscometer equipped with an "MS-r4" rotor at a frequency of 60 Hz.

* * * * *